United States Patent
Schiller et al.

(10) Patent No.: US 8,848,929 B2
(45) Date of Patent: Sep. 30, 2014

(54) SOUND EXPOSURE MONITORING SYSTEM AND METHOD FOR OPERATING THE SAME

(75) Inventors: Ean H. Schiller, Christiansburg, VA (US); Jonathan M. Hager, Salem, VA (US)

(73) Assignee: AEGISOUND, Christiansburg, VA (US)

( * ) Notice: Subject to any disclaimer, the term of this patent is extended or adjusted under 35 U.S.C. 154(b) by 303 days.

(21) Appl. No.: 13/488,949

(22) Filed: Jun. 5, 2012

(65) Prior Publication Data

US 2012/0321094 A1    Dec. 20, 2012

Related U.S. Application Data (60) Provisional application No. 61/496,642, filed on Jun. 14, 2011.

(51) Int. Cl.
*H04R 29/00* (2006.01)
*G01H 3/14* (2006.01)

(52) U.S. Cl.
CPC ...................................... *G01H 3/14* (2013.01)
USPC ................ 381/56; 455/414.1; 381/315

(58) Field of Classification Search
USPC ................. 381/56, 315, 60, 328; 455/414.1
See application file for complete search history.

(56) References Cited

U.S. PATENT DOCUMENTS

| | | | |
|---|---|---|---|
| 5,577,511 A | 11/1996 | Killion | |
| 5,757,930 A | 5/1998 | Seidemann et al. | |
| 6,223,090 B1 * | 4/2001 | Brungart | 700/28 |
| 6,456,199 B1 | 9/2002 | Michael | |
| 6,687,377 B2 | 2/2004 | Voix et al. | |
| 6,754,359 B1 | 6/2004 | Svean et al. | |
| 6,826,515 B2 | 11/2004 | Bernardi et al. | |
| 6,898,290 B1 | 5/2005 | Saunders et al. | |
| 7,024,010 B2 | 4/2006 | Saunders et al. | |
| 7,110,551 B1 | 9/2006 | Saunders et al. | |
| 7,151,835 B2 | 12/2006 | Yonovitz et al. | |
| 7,289,636 B2 | 10/2007 | Saunders et al. | |
| 7,319,399 B2 | 1/2008 | Berg | |
| 7,688,983 B2 | 3/2010 | Voix et al. | |
| 7,817,803 B2 | 10/2010 | Goldstein | |
| 7,836,770 B2 | 11/2010 | Goldberg et al. | |
| 7,836,771 B2 | 11/2010 | Killion | |
| 7,882,743 B2 | 2/2011 | Goldberg et al. | |
| 2003/0191609 A1 | 10/2003 | Bernardi et al. | |
| 2005/0244013 A1 | 11/2005 | Battenberg et al. | |
| 2005/0254667 A1 | 11/2005 | Michael | |
| 2007/0272022 A1 * | 11/2007 | Sivonen et al. | 73/646 |
| 2009/0238370 A1 * | 9/2009 | Rumsey et al. | 381/58 |
| 2010/0046767 A1 | 2/2010 | Bayley et al. | |
| 2010/0142719 A1 * | 6/2010 | Chiba et al. | 381/71.6 |
| 2011/0058680 A1 | 3/2011 | Michael | |

* cited by examiner

*Primary Examiner* — Creighton Smith
(74) *Attorney, Agent, or Firm* — The Marbury Law Group, PLLC (57) ABSTRACT

A personal noise monitoring system and method for operating the same. Sound pressure data from inside the ears of a user of hearing protection device (HPD) are acquired from microphones in the HPD and reported to a master control unit. Simultaneously, the master control unit receives sound pressure data from the ambient environment in which the user is located. The data are reported to a central server for processing. The central server may use the data to determine in near real time or real time whether the user of the HPD is at risk for exposure to excess sound levels and to take remedial action while the user is still in the ambient environment.

23 Claims, 10 Drawing Sheets

SOUND EXPOSURE MONITORING SYSTEM AND METHOD FOR OPERATING THE SAME

CROSS REFERENCE TO RELATED APPLICATIONS

This application claims priority under 35 U.S.C. §119(e) from provisional application No. 61/496,642 filed Jun. 14, 2011. The 61/486,642 provisional application is incorporated by reference herein, in its entirety, for all purposes.

BACKGROUND

Noise induced hearing loss (NIHL) is still a problem throughout the military battlespace and civilian manufacturing sectors. High performance hearing protection devices (HPDs) are available. However, HPDs do not reliably detect changes in noise levels that occur between conventional periodic noise monitoring events. Additionally, there are few means for evaluating the adequacy of a person's hearing protection, or for detecting and enforcing compliance with hearing conservation directives.

Knowledge of noise exposure in real-time or near real-time allows for intervention before a compliance issue arises and/or before hearing loss occurs. For example, if it were known that an individual is not wearing hearing protection or wearing it incorrectly, the reasons could be ascertained and the problem corrected. If it were known which HPDs are underperforming, then those devices could be replaced. If it were known that an individual has exceeded his or her safe daily noise exposure, then that individual could be moved to a quieter environment.

SUMMARY

Embodiments are directed to a personal sound exposure monitoring system and method for operating such a system.

In one embodiment, a system for monitoring sound exposure includes a hearing protection device and a master control unit. The hearing protection device utilizes first and second microphones for measuring sound pressure in the ears of a user. The master control unit includes a third microphone, a wireless communications system, a first processor, first software executable instructions, and a unique identifier stored in a memory. The first processor is configured with software executable instructions that when executed cause the master control unit to perform various operations. For example, master control unit may receive sound measurement data from the first, second and third microphones and associate the sound measurement data with the unique identifier stored in the memory. The sound measurement data and the unique identifier may be sent to a central server via the communication system. In another embodiment, the master control unit may issue alerts. By way of illustration and not by way of limitation, the master control unit may issue alerts when the sound measurement data indicates that the hearing protection device is not being used or is being incorrectly used by the user, when the sound measurement data indicates that the master control unit is present in a high noise environment requiring the use of the hearing protection device, and when the sound measurement data indicates that additional hearing protection measures are required.

The central server may utilize a second processor configured with software executable instructions that when executed cause the central server to perform various operations. For example, the central server may continuously determining a sound exposure measure from the sound measurement data associated with the unique identifier and may issue an alert when the sound exposure measure indicates that an alert should be sent. By way of illustration and not by way of limitation, the central server may issue alerts when the sound measurement data indicates that the hearing protection device is not being used or is being incorrectly used by the user, when the sound measurement data indicates that the master control unit is present in a high noise environment requiring the use of the hearing protection device, and when the sound measurement data indicates that additional hearing protection measures are required.

In another embodiment, the central server may also determine a threshold level for the user based on the user information or historical exposure data. The historical exposure data may be projected to a future time to establish the current threshold level for the user. In still another embodiment, the central server may compare the exposure measure of an individual to one or more sound exposure guidelines.

DETAILED DESCRIPTION

Embodiments are directed to a sound exposure monitoring system and method for operating such a system and to a personal monitoring subsystem.

Figure 1:
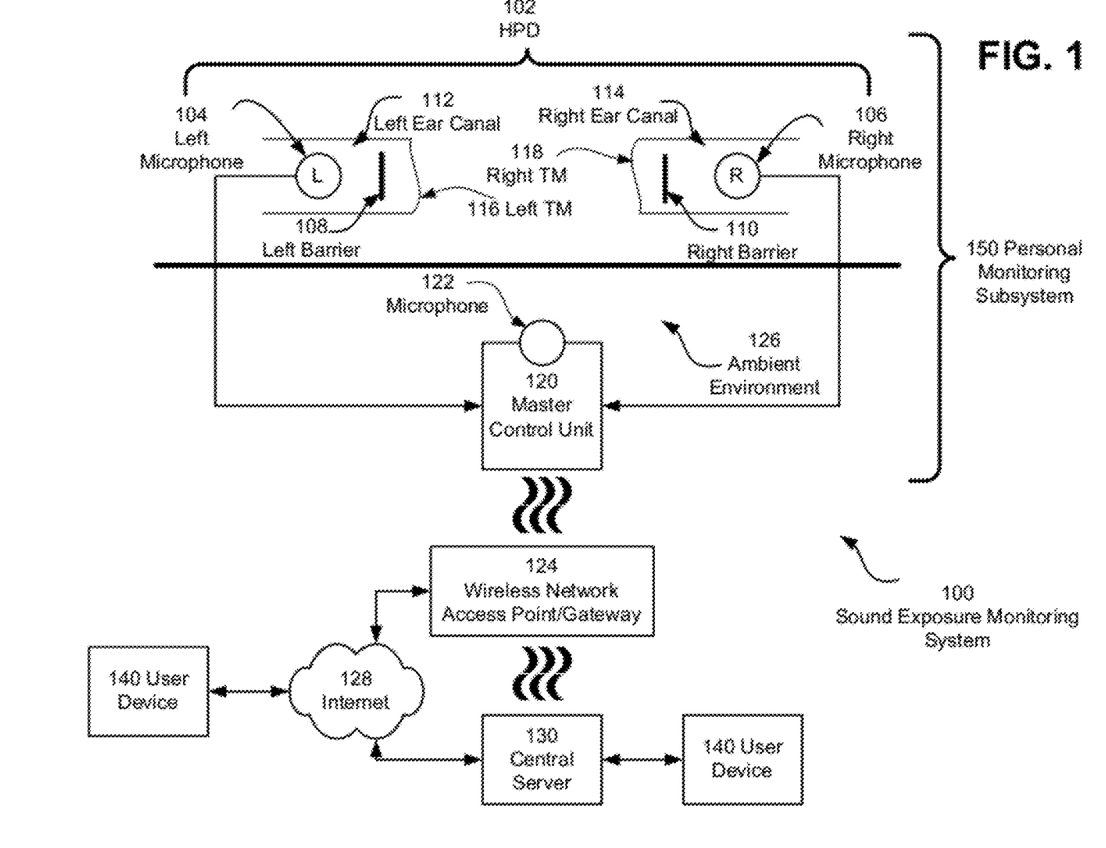
FIG. 1 is a block diagram illustrating a sound exposure monitoring system according to an embodiment.

As illustrated in FIG. 1, a sound exposure monitoring system 100 comprises a hearing protection device (HPD) 102, a master control unit 120, and a central server 130. The HPD 102 comprises left microphone 104 and right microphone 106. The HPD 102 may be in the form of a circumaural earmuff, insert hearing protector, or combination of both and among others and may provide both passive and active noise suppression, or either. The microphones 104 and 106 of the HPD 102 measure the sound pressure inside the left ear canal 112 and the right ear canal 114 of the user. In an embodiment, an optional barrier (108 and 110) may be interposed between the microphones 104 and 106 and the tympanic membrane (116 and 118). The optional barriers 108 and 110 may be in the form of a wax guard, wax screen, moisture guard, grating, film, membrane, semi-permeable screen, acoustic or physical filter.

The microphones 104 and 106 of the HPD 102 are in communication with a master control unit 120. Together, HPD 102 and master control unit 120 form a personal monitoring subsystem 150. The personal monitoring subsystem 150 is worn by a user. As will be illustrated in more detail below, the data from the personal monitoring subsystem 150 of any number of users may be monitored by a central server 130. In an embodiment, the user of the personal monitoring subsystem 150 does not monitor that user's sound exposure but relies on a user of the central server 130 to determine whether remedial action is warranted. In another embodiment, the master control unit 120 may be configured to alert the user that the user is in a noisy environment that requires the use of hearing protection. In yet another embodiment, the central server 130 may be configured to issue warning signals to the master control unit 120 when the central server determines that the user is in a noisy environment that requires the user to utilize hearing protection or that the user has exceeded an exposure measure. In yet another embodiment, the data from the personal monitoring subsystem 150 is monitoring following the alert to determine whether the alert was received or, if received, ignored. In the event that data from the personal monitoring system that is received subsequent to an alert indicates that the reason for the alert has not been addressed, other actions may be taken.

In the discussion that follows the term "user" refers to a person wearing a personal monitoring subsystem 150 and the term "administrator" refers to a person who monitors the exposure of the user via access to the central server 130.

The master control unit 120 communicates over a wireless network 124 via an access point or gateway with a central server 130. By way of illustration and not by way of limitation, wireless network 124 may be a WiFi network, or a cellular network among others. Central server 130 may comprise an interface with the wireless network access point 124 to connect to the master control unit 120. In an alternative embodiment, the wireless network may terminate in a gateway or router 124 that interfaces wireless network 124 with the Internet 128. In this embodiment, the central server 130 may be a web server that is accessible to a user device 140 via a web browser. The user device 140 may connect to the central server 130 through a local network or via the Internet 128.

In an embodiment, the user device may be a computer, a tablet or a smart phone.

Figure 2:
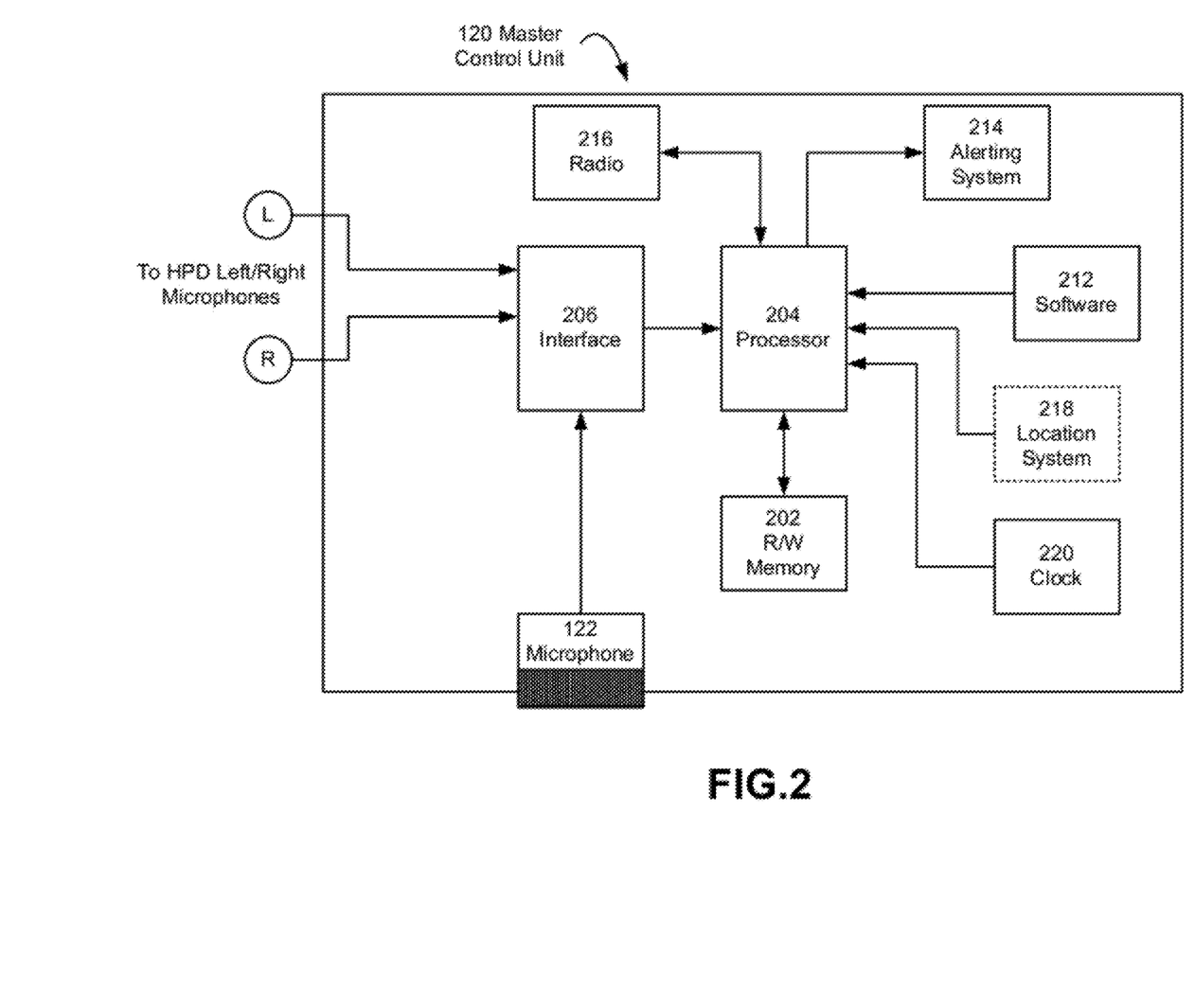
FIG. 2 is a block diagram illustrating a master control unit of a personal monitoring subsystem according to an embodiment.

FIG. 2 is a block diagram illustrating a master control unit of a personal monitoring subsystem according to an embodiment.

In an embodiment, the master control unit 120 comprises a microphone 122, a read/write memory 202, a processor 204, an interface 206, software 212, an alerting system 214 and a radio 216. An optional location system 218 is also illustrated. The master control unit 120 may further comprise additional circuits for interconnecting the various components and systems of master control unit 120, power systems and structural elements.

In an embodiment the master control unit 120 is integrated into, contained within, or attached to, the HPD 102.

The processor 204 simultaneously (or nearly simultaneously) receives signals from the left and right microphones (104 and 106) of the HPD 102 and signals from microphone 122. As illustrated in FIG. 1, left and right microphones 104 and 106 are located in the ear canals 112 and 114 of a user of the HPD and measure the sound pressure inside of the ear canals 112 and 114. The master control unit 120 is worn by a user and is fully exposed to an ambient environment 126. The microphone 122 is configured to measure the sound pressure of the ambient environment 126. The data from microphones 104, 106 and 122 may be used by the master control unit 120 to identify locations in which hearing protection is required. The master control unit 120 may use the alerting system 214 to alert the user of the personal monitoring system 150 that the user is in an environment where the sound levels are high and warrant wearing hearing protection. An alert may be in the form of an illuminated or flashing warning light for the user to see or a vibrating actuator for the user to feel.

The signals from the microphones 104 and 106 of the HPD 102 as well as signals from microphone 122 are simultaneously (or nearly simultaneously) received at interface 206. The interface 206 may condition the analog signals before converting to digital signals for processing by the processor 204. For example, the interface 206 may remove artifacts in the signal induced by electromagnetic interference (EMI) or direct current (DC) bias or offsets.

The processor 204 executes instructions from software 212 to read the digital data representing the signals received from the microphones 104, 106 and 122 to read/write memory 202. The data may be associated with a measurement time determined by a clock 220. The data may also be associated with an identifier that is uniquely assigned to a personal monitoring subsystem 150. The identifier may be associated with a user of the personal monitoring subsystem 150 in a database of the central server 130. Additionally, the processor 204 may shape the digital signals to compensate for acoustic effects in the microphone responses caused by the presence of the optional barriers 108 and 110. Since barriers can alter the resonances in an acoustic system, in an embodiment the processor 204 account for those resonances when calculating sound pressure levels and noise exposures. For example, the processor 204 may apply correction filters to flatten the frequency response prior to applying A-weighting filters, digital infinite impulse response filters, exponential time averaging, logarithmic encoding, or other frequency or temporal weighting algorithms to the data.

In an embodiment, the software instructions from software 212 may also cause the processor 204 to periodically read data from the read/write memory 202, turn on radio 216 and broadcast the data over wireless network 124. In another embodiment, the reporting interval is determined by an operator of the sound exposure monitoring system 100. In still another embodiment, the reporting interval may be adjusted by signals sent from the central server 130. In another embodiment, once data has been sent, the software 212 turns off radio 216 to conserve battery life.

The master control unit 120 receives signals from microphones 104, 106 and 122 simultaneously (or nearly simultaneously). The personal monitoring subsystem 150 reports the status of a user continuously in near real-time to the central server 130. As the interval chosen for reporting data stored in read/write memory 202 is reduced, the reporting approaches real-time.

In an embodiment, when the personal monitoring subsystem 150 is distant from or does not have access to the wireless network 124, the master control unit stores data collected from microphones 104, 106 and 122 in the read/write memory 202. At such time that the personal monitoring subsystem 150 again has access to the wireless network 124, the master control unit transfers the data stored in read/write memory 202 to the central server 130. In this way, data is collected at all times that the personal monitoring subsystem 150 is in use, and the central server 130 receives status updates in near real-time at all times that the wireless network 124 is accessible to the personal monitoring subsystem 150.

In an embodiment, the location of the master control unit 120 is determined by a location system 118. By way of illustration and not by way of limitation, the location system may be a GPS-based system, an RFID-based system, a wireless node array or a Bluetooth-based system. Location data may be acquired from the location system 118 and stored in association with the data from the microphones 104, 106 and 122. Location data may also be computed by central server 118 by applying signal triangulation techniques to transmissions from radio 216. The location data may be used by the master control unit 120 to identify locations in which hearing protection is required. The master control unit 120 may use the alerting system 214 to alert the user of the personal monitoring system 150 that the user has entered a hearing protection area.

Figure 3:
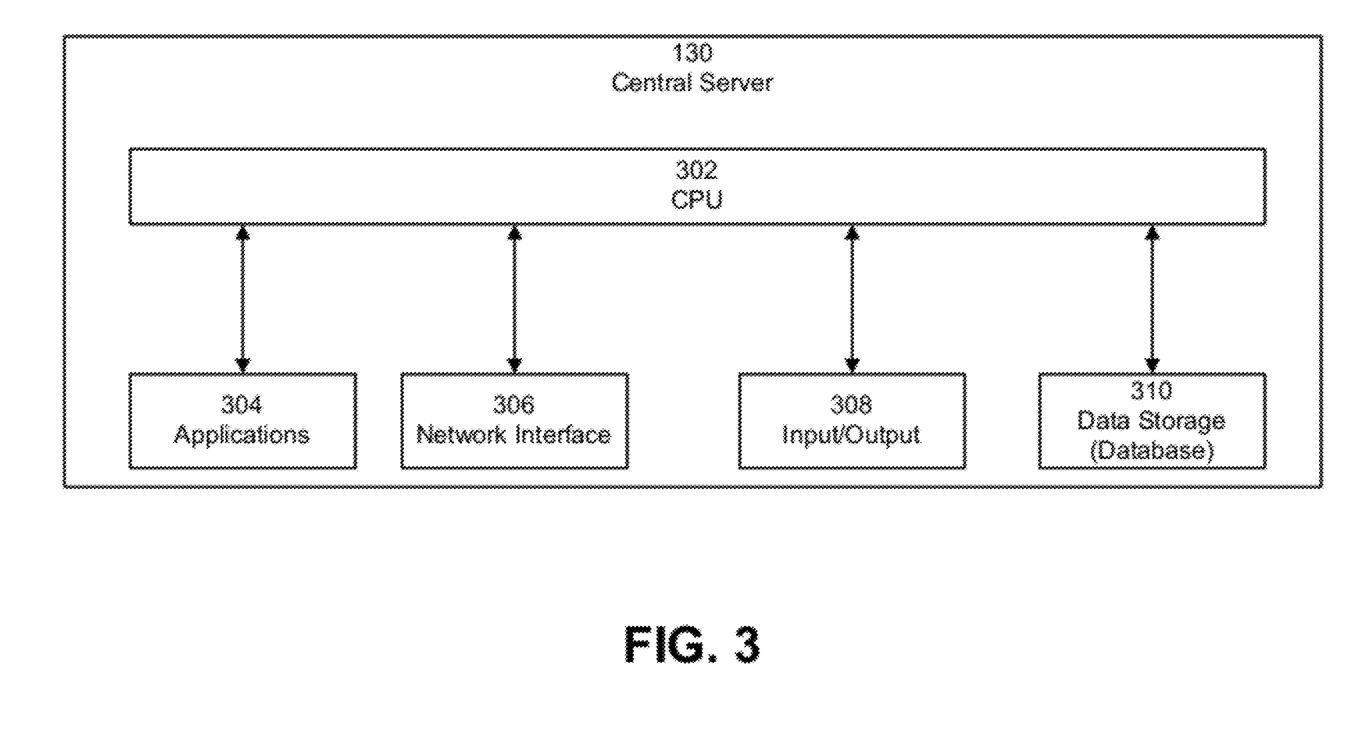
FIG. 3 is a block diagram illustrating a central server of a sound exposure monitoring system according to an embodiment.

FIG. 3 is a block diagram illustrating a central server of a sound exposure monitoring system according to an embodiment.

As illustrated in FIG. 3, the central server 130 comprises a CPU 302, applications 304, a network interface 306, an input/output system 308 and a data storage system 310. Data relating to the signals at the microphones 104, 106 and 122 sent from the master control unit 120 are received by the central server 130 via the network interface.

The network interface 306 may provide a direct connection to wireless network AP/Gateway 124 or an interface to the Internet 128. The network interface 306 may further provide access to an administrator via a remote user device 140 configured as a client to central server 130. In an embodiment, the remote user device 140 interacts with central server 130 via the Internet.

The input/output system allows an administrator using the central server 130 to interact with applications 304. The CPU 302 executes instructions from the applications stored at block 304 and processes the data. The applications 304 may include instructions for evaluating the data received from one or more personal monitoring subsystems 150. Additionally, the CPU 302 may apply signal shaping to the digital data received from the master control unit 120 to compensate for the acoustic effects in the microphone response induced by the presence of the optional barriers 108 and 110 when this compensation is not performed by the master control unit 120.

In an embodiment, the unique identifier of a personal monitoring subsystem 150 is associated with a user in the data storage system 310. The data from the microphones 104, 106 and 122 sent from a personal monitoring subsystem 150 to the central server include the unique identifier of the personal monitoring subsystem 150. In this way, the central server may associate monitoring data from multiple personal monitoring subsystems 150 with individual users. Data storage system 310 may also store information about the user of each personal monitoring subsystem 150. By way of illustration and not by way of limitation, the information about a user may include the state of the user's hearing, the start time, end time and length of the user's shift, the noise exposure limits applicable to that user, and the location to which the user has been assigned. In an embodiment, the information about the user may be used to provide a custom sound exposure threshold for each user of a personal monitoring subsystem 150.

The data may be processed using one or more applications 304 to determine which users are safely operating in an ambient environment and which users are approaching an exposure limit. In this way, action may be taken by an administrator before a user of an HPD has been exposed to potentially damaging sound levels and before a shift has ended.

The following examples illustrate how the data received at the central server 130 may be used by an administrator to monitor and protect users of one or more personal monitoring subsystems 150.

Example 1

| In Ear Data: | 75 dB SPL, 15% dose |
|---|---|
| Exterior Data: | 105 dB SPL |
| Status: | OK |
| Analysis: | In-ear levels OK |
| | In-ear is 30 dB less than exterior |
| | Earplugs are working |
| | No action required |

In example 1, the exposure of a user is 15% of a maximum dose. Because of the difference between the in-the-ear sound levels and the ambient environment levels, the user is also wearing the HPD correctly. No action is required and no alert is issued.

Example 2

| In Ear Data: | 90 dB SPL, 56% dose |
|---|---|
| Exterior Data: | 105 dB SPL |
| Status: | Caution |
| Analysis: | In-ear levels high |
| | In-ear is only 15 dB less than exterior |
| | Poor fit or bad earplugs |
| | Retrain client or refit earplugs |

In example 2, the exposure of a user is 56% of a maximum dose. Because of the difference between the in-the-ear sound levels and the ambient environment levels is minimal (15 dB), the user may not be wearing the HPD correctly or it may not fit correctly. Non-urgent action is required. An alert may be issued to the administrator by the central server 130.

Example 3

| In Ear Data: | 105 dB SPL, 97% dose |
|---|---|
| Exterior Data: | 105 dB SPL |
| Status: | Danger |
| Analysis: | In-ear levels very high |
| | In-ear level equals exterior level |
| | Likely that earplugs are not being used |
| | Remove client from location; retrain |

In example 3, the sound levels measure by the HDP microphones is the same as the sound level measured by the microphone in master control unit 120. The exposure of a user is 97% of a maximum dose user. Immediate action is required. In an embodiment, an alert may be issued to the administrator by the central server 130 when the sound exposure of an individual user reaches a threshold level. The threshold level may be expressed as a percentage of a pre-determined dose. In another embodiment, the threshold level may be determined for each individual user of a personal monitoring subsystem 150 based on information about the user that is stored in the data storage system 310. In yet another embodiment, the threshold may be dynamically established based on a future projection of previously acquired exposure data. In another embodiment, an alert may also be issued to the user of the personal monitoring subsystem 150 via alerting system 214.

The data from the personal monitoring subsystems 150 may be displayed in various ways and on various devices. FIGS. 4-10 illustrate various displays generated by the central server 130.

Figure 4:
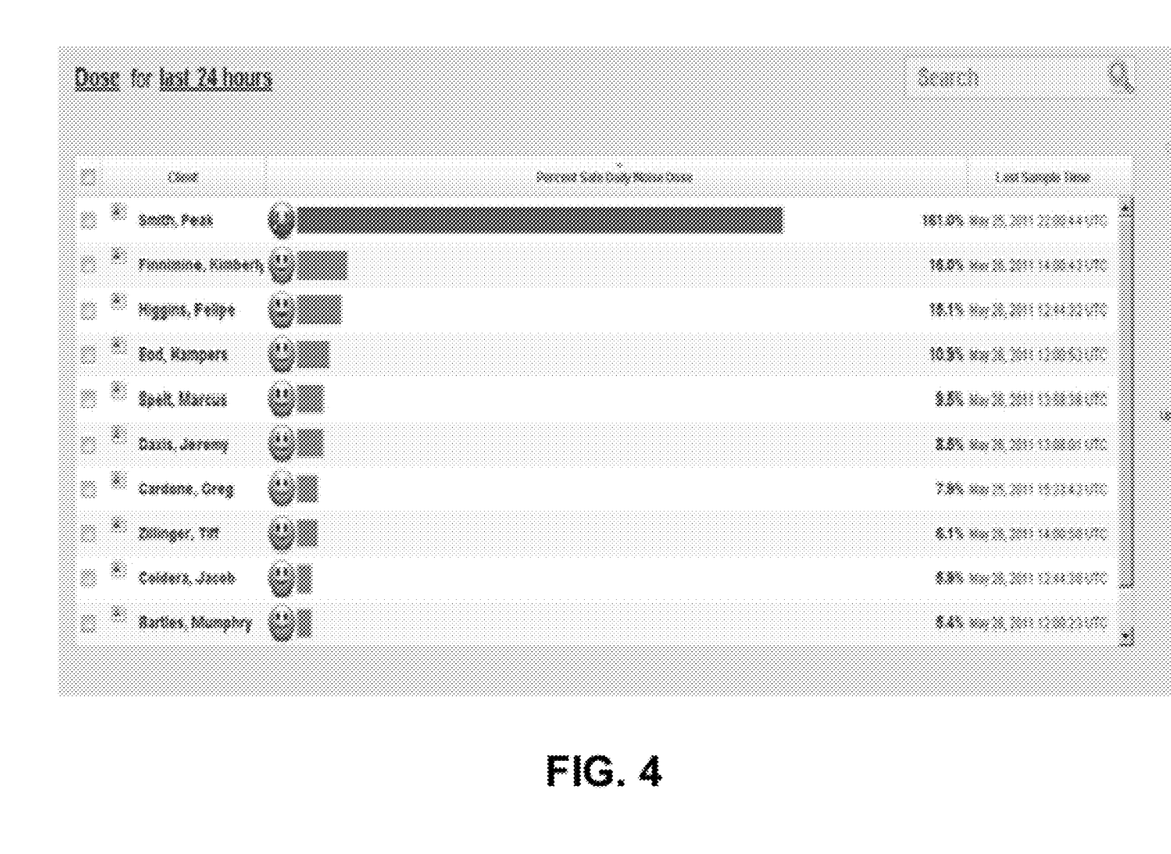
FIGS. 4-10 illustrate various displays generated by the central server 130 according to embodiments.

FIG. 4 is a bar chart illustrating dosing levels for a group of users of personal monitoring subsystems 150. As illustrated in FIG. 4, dosing that is below threshold levels is assigned a green color and dosing that exceeds a threshold level is assigned a red color.

Figure 5:
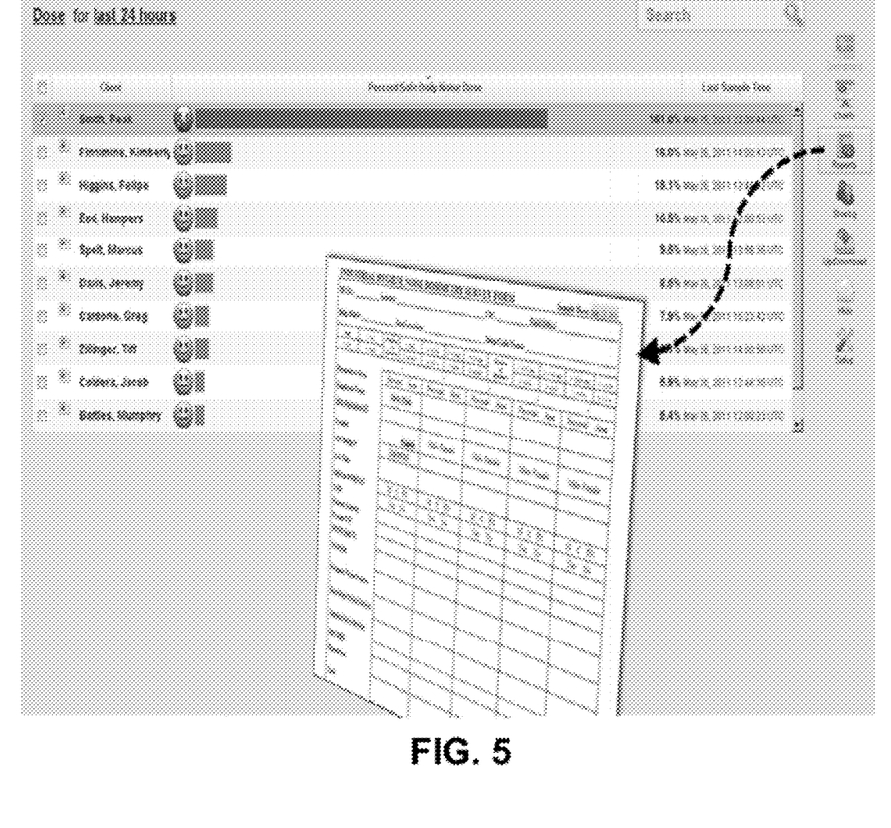

FIG. 5 illustrates a reporting function that may be used in conjunction with the dosing bar chart of FIG. 4 to populate a form with data.

Figure 6:
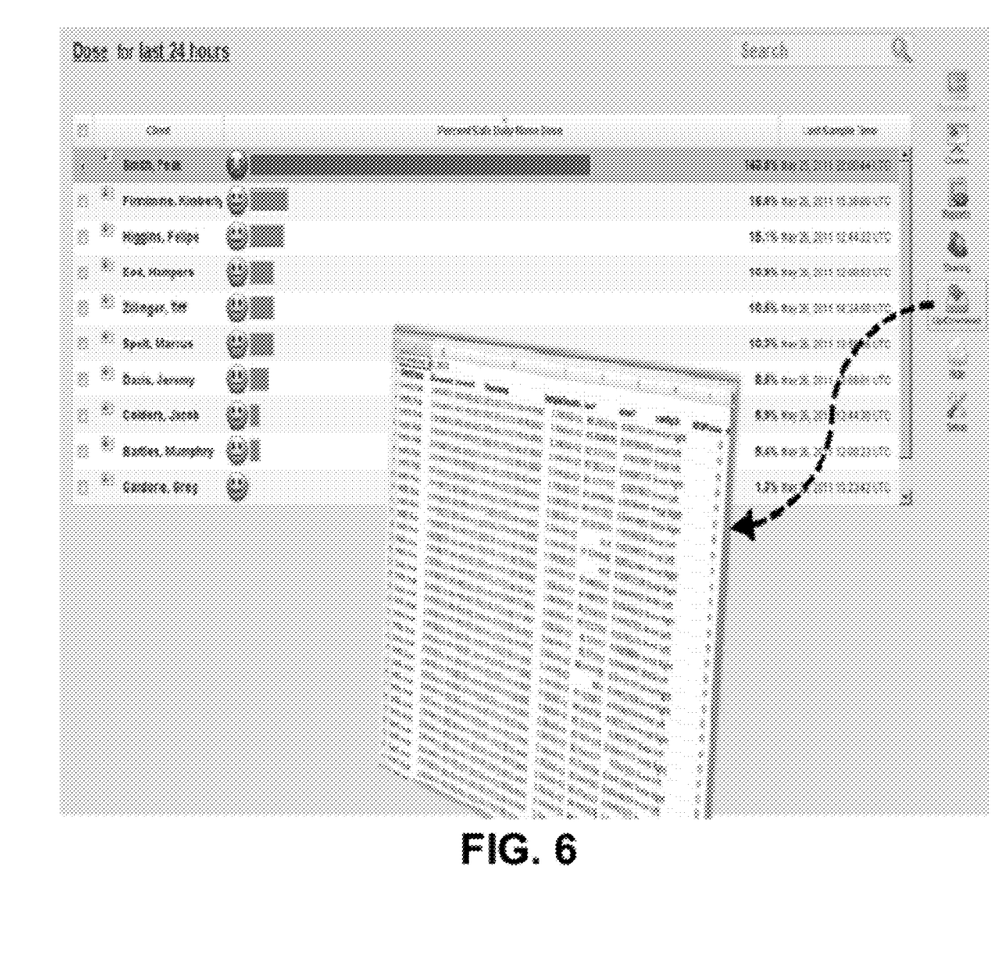

FIG. 6 illustrates a reporting function that may be used in conjunction with the dosing bar chart of FIG. 4 to populate a spreadsheet with data.

Figure 7:
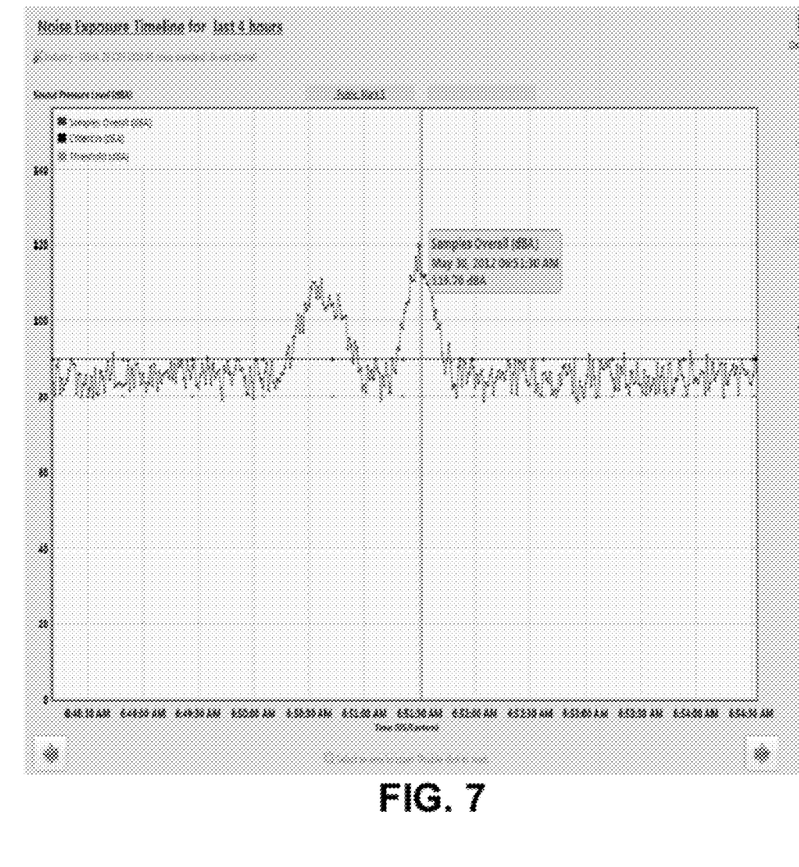

FIG. 7 illustrates a noise data time line for a particular user of a particular personal monitoring subsystem 150 that is generated by an application 304 operating on the central server 130. The application 304 operates on the accumulated exposure data that is stored in the data storage system 310 in association with the particular user.

Figure 8:
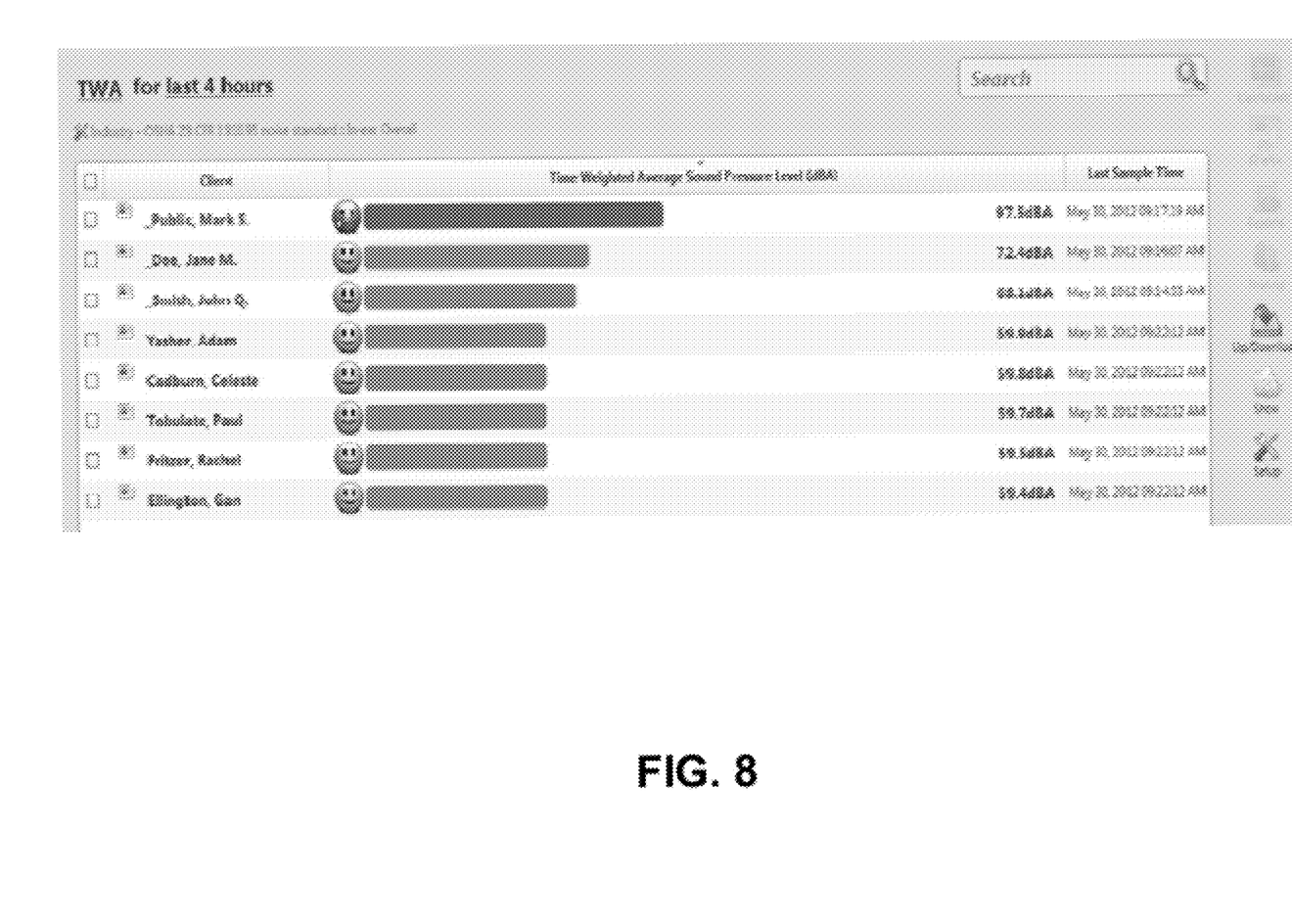

FIG. 8 illustrates a time-weighted average exposure for a group of users of personal monitoring subsystems 150 that is generated by an application 304 operating on the central server 130. The application 304 operates on the accumulated exposure data that is stored in the data storage system 310 in association with each member of the group.

Figure 9:
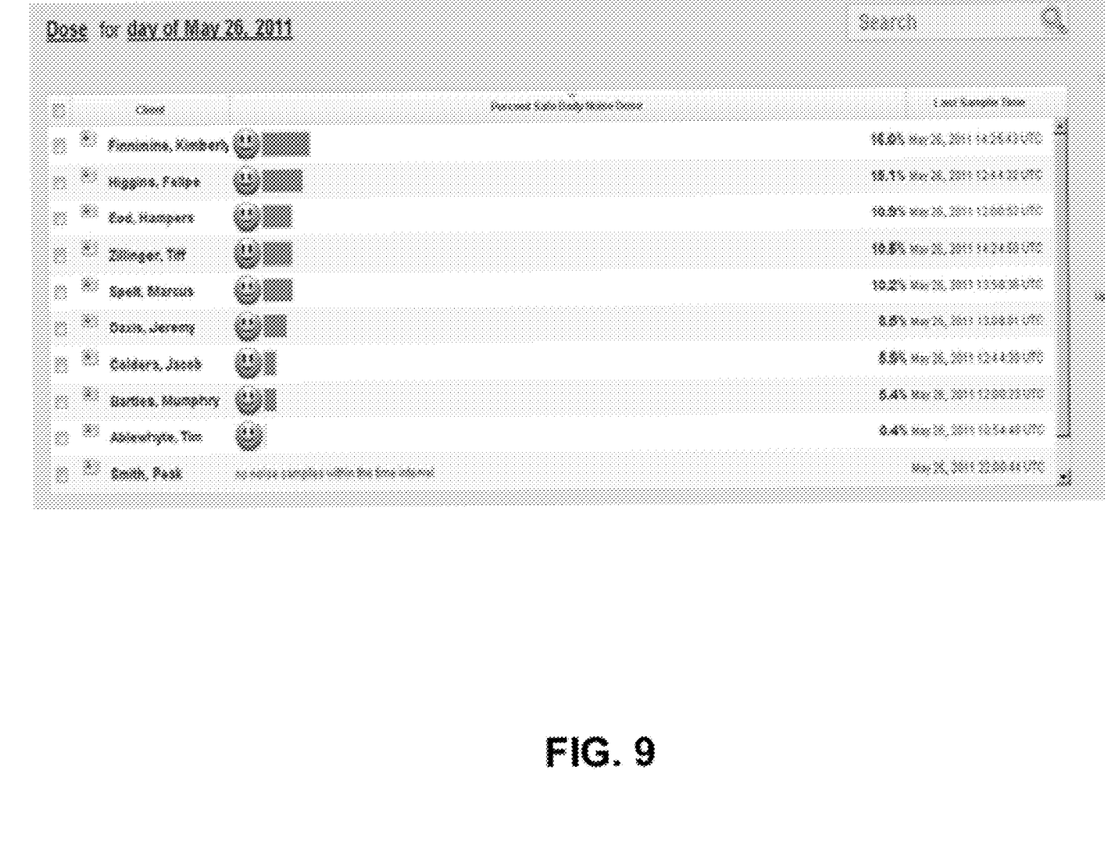

FIG. 9 illustrates historical exposure for a particular data for a group of users of personal monitoring subsystems 150 that is generated by an application 304 operating on the central server 130. The application 304 operates on the accumulated exposure data that is stored in the data storage system 310 in association with each member of the group.

Figure 10:
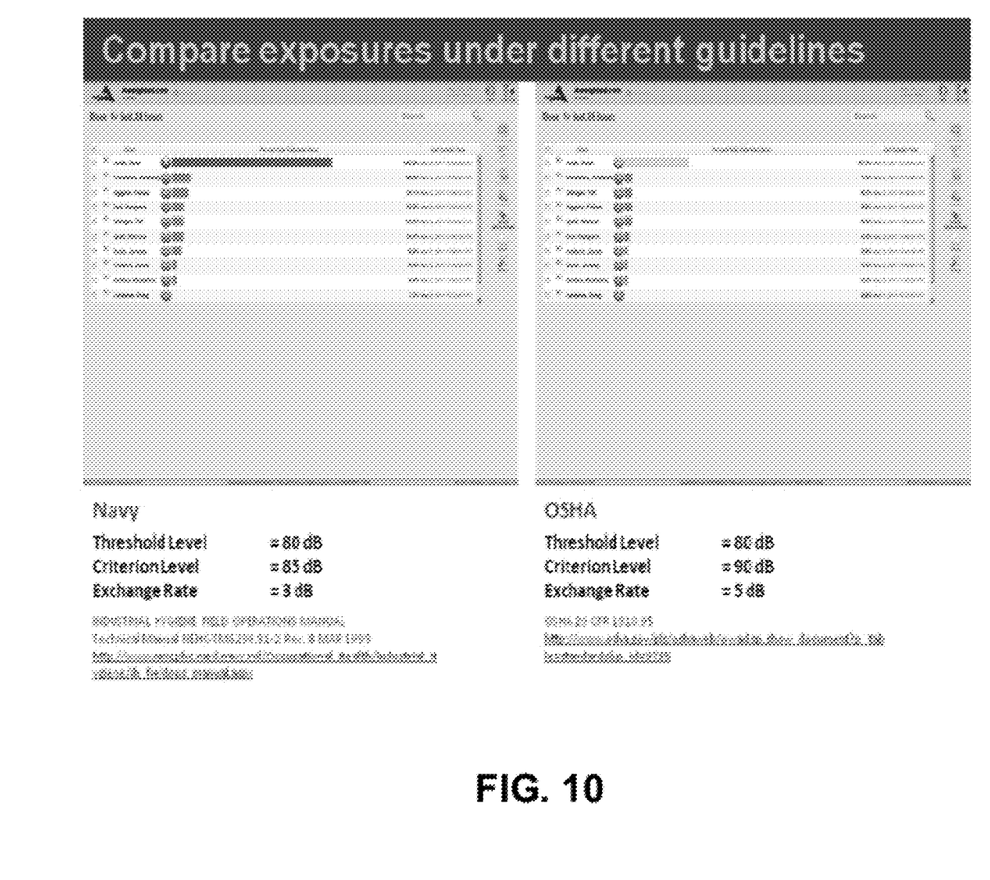

FIG. 10 illustrates a comparison of the exposure for a group of users of personal monitoring subsystems 150 according to different noise guidelines that is generated by an application 304 operating on the central server 130. The application 304 operates on the accumulated exposure data that is stored in the data storage system 310 in association with each member of the group and the guidelines that are also stored in data storage system 310. While FIG. 10 illustrates two different guidelines, other guidelines may be used. For example, exposures may be compared to guidelines issued by the U.S. Occupational Safety and Health Administration (OSHA), the U.S. Mine Safety and Health Administration (MSHA), the U.S. National Institute for Occupational Safety and Health (NIOSH), the U.S. Environmental Protection Agency, the U.S. Department of Defense, the U.S. Department of the Navy, the American National Standards Institute (ANSI), and the International Organization for Standardization (ISO).

Other applications are possible. For example, where location data is collected with data from microphones 104, 106 and 122, analysis of the sound levels in a work environment may be collected and evaluated against expected sound levels. These data may also be used for sound mapping of a work environment and also provide remote monitoring of equipment or other noise sources where sound levels greater than expected could indicate a problem requiring remedial action.

In another embodiment, data from personal monitoring systems that are operating in common area may be evaluated to determine a noise level measure for the common area. Data from individual personal monitoring systems may be compared to the noise level measure to determine whether any particular personal monitoring system requires calibration or whether a correction factor needs to be applied to data received from the particular device to correct for over or under sensitivity.

The foregoing method descriptions and the process flow diagrams are provided merely as illustrative examples and are not intended to require or imply that the blocks of the various embodiments must be performed in the order presented. As will be appreciated by one of skill in the art the order of blocks in the foregoing embodiments may be performed in any order. Words such as "thereafter," "then," "next," etc. are not intended to limit the order of the blocks; these words are simply used to guide the reader through the description of the methods. Further, any reference to claim elements in the singular, for example, using the articles "a," "an," or "the," is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some blocks or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The blocks of a method or algorithm disclosed herein may be embodied in a processor-executable software module, which may reside on a computer-readable medium. Computer-readable media includes both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a machine readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. Thus, the present invention is not intended to be limited to the embodiments shown herein but is to be accorded the widest scope consistent with the following claims and the principles and novel features disclosed herein.

What is claimed is:

1. A system for monitoring sound exposure comprising:
a hearing protection device, wherein the hearing protection device comprises first and second microphones for measuring sound pressure in the ears of a user;
a master control unit, wherein the master control unit comprises a third microphone, a wireless communications system, a first processor, first software executable instructions, and a unique identifier stored in a memory, and wherein the first processor is configured with software executable instructions to cause the master control unit to perform operations comprising:
receiving sound measurement data from the first, second and third microphones;
associating the sound measurement data with the unique identifier stored in the memory; and
sending the sound measurement data and the unique identifier to a central server via the communication system, wherein
the central server comprises a second processor and second software executable instructions and wherein the second processor is configured with the second software executable instructions to cause the central server to perform operations comprising:
continuously determining a sound exposure measure from the sound measurement data associated with the unique identifier; and
issuing an alert when the sound exposure measure indicates that an alert should be sent.

2. The system of claim 1 further comprising a data storage unit, wherein the data storage unit comprises user information associated with the unique identifier, and wherein the second processor is configured with the second software executable instructions to cause the central server to perform operations further comprising determining a threshold level for the user based on the user information.

3. The system of claim 2, wherein the user information is selected from group consisting of a measure of a state of hearing of the user, an exposure start time, an exposure end time, a length of the user's shift, the noise exposure limits applicable to that user, and a location to which the user has been assigned.

4. The system of claim 1 further comprising a data storage unit, wherein the data storage unit comprises historical exposure data associated with the unique identifier, and wherein the second processor is configured with the second software executable instructions to cause the central server to perform operations further comprising determining a threshold level for the user based on the historical exposure data.

5. The system of claim 4 further comprising a data storage unit, wherein the threshold is established using a projection of the historical exposure data to a future time.

6. The system of claim 1 further comprising a data storage unit, wherein the data storage unit comprises accumulated exposure data associated with unique identifier, and wherein the second processor is configured with the second software executable instructions to cause the central server to perform operations further comprising comparing the sound exposure measure to one more sound exposure guidelines.

7. The system of claim 6, wherein the one or more sound exposure guidelines are selected from the group consisting of guidelines issued by the U.S. Occupational Safety and Health Administration (OSHA), the U.S. Mine Safety and Health Administration (MSHA), the U.S. National Institute for Occupational Safety and Health (NIOSH), the U.S. Environmental Protection Agency, the U.S. Department of Defense, the U.S. Department of the Navy, the American National Standards Institute (ANSI), and the International Organization for Standardization (ISO).

8. The system of claim 1 further comprising, wherein first microphone is positioned in a left ear canal of the user and second microphone is position in a right ear canal of the user, and wherein the system further comprises a first barrier situated between the first microphone and a left tympanic membrane and a second barrier situated between the second microphone and a right tympanic membrane.

9. The system of claim 8, wherein barrier is selected from the group consisting of a wax guard, a wax screen, a moisture guard, a grating, a film, a membrane, a semi-permeable screen, and an acoustic or physical filter.

10. The system of claim 8, wherein the first processor is configured with the first software executable instructions to cause the master control unit to perform operations further comprising shaping the sound measurement data from the first and second microphones to compensate for changes in the sound measurement induced by the presence of the first and second barriers.

11. The system of claim 8, wherein the second processor is configured with the second software executable instructions to cause the central server to perform operations further comprising shaping the sound measurement data from the first and second microphones to compensate for changes in the sound measurement induced by the presence of the first and second barriers.

12. The system of claim 1, wherein the first processor is configured with the first software executable instructions to cause the master control unit to perform operations further comprising:
shaping the sound measurement data from the first and second microphones; and
determining from the shaped sound measurement data a risk of hearing damage posed by the sound measurement from the first and second microphones.

13. The system of claim 1, wherein the second processor is configured with the second software executable instructions to cause the central server to perform operations further comprising:
shaping the sound measurement data from the first and second microphones; and
determining from the shaped sound measurement data a risk of hearing damage posed by the sound measurement from the first and second microphones.

14. The system of claim 1, wherein first microphone is positioned in a left ear canal of the user and second microphone is position in a right ear canal of the user, and, wherein the first processor is configured with the first software executable instructions to cause the master control unit to perform operations further comprising:
shaping the sound measurement data from the first and second microphones; and
determining from the shaped sound measurement data a measure of sound pressure on at least one of a left tympanic membrane and a right tympanic membrane.

15. The system of claim 1, wherein first microphone is positioned in a left ear canal of the user and second microphone is position in a right ear canal of the user, and, wherein the second processor is configured with the second software executable instructions to cause the central server to perform operations further comprising:
  shaping the sound measurement data from the first and second microphones; and
  determining from the shaped sound measurement data measure of sound pressure on at least one of a left tympanic membrane and a right tympanic membrane.

16. The system of claim 1, wherein the first processor is configured with the first software executable instructions to cause the master control unit to perform operations further comprising:
  comparing the sound measurement data from the first, second and third microphones; and
  issuing an alert when the sound measurement data indicates that the hearing protection device is not being used or is being incorrectly used by the user.

17. The system of claim 1, wherein the operation of the central server of issuing an alert when the sound exposure measure indicates than an alert should be sent comprises:
  comparing the sound measurement data from the first, second and third microphones; and
  issuing an alert when the sound measurement data indicates that the hearing protection device is not being used or is being incorrectly used by the user.

18. The system of claim 1, wherein the first processor is configured with the first software executable instructions to cause the master control unit to perform operations further comprising:
  comparing the sound measurement data from the first, second and third microphones; and
  determining from the sound measurement data a measure of sound attenuation provided by the hearing protection device.

19. The system of claim 1, wherein the second processor is configured with the second software executable instructions to cause the central server to perform operations further comprising:
  comparing the sound measurement data from the first, second and third microphones; and
  determining from the sound measurement data a measure of sound attenuation provided by the hearing protection device.

20. The system of claim 1, wherein the first processor is configured with the first software executable instructions to cause the master control unit to perform operations further comprising:
  comparing the sound measurement data from the first, second and third microphones;
  determining from the sound measurement data whether the master control unit is present in a high noise environment requiring the use of the hearing protection device; and
  issuing an alert when the master control unit is present in a high noise environment requiring the use of the hearing protection device.

21. The system of claim 1, wherein the operation of the central server of issuing an alert when the sound exposure measure indicates than an alert should be sent comprises:
  comparing the sound measurement data from the first, second and third microphones;
  determining from the sound measurement data whether the master control unit is present in a high noise environment requiring the use of the hearing protection device; and
  issuing an alert to the master control unit when the master control unit is present in a high noise environment requiring the use of the hearing protection device.

22. The system of claim 1, wherein the operation of the central server of issuing an alert when the sound exposure measure indicates than an alert should be sent comprises issuing an alert to the master control unit.

23. The system of claim 1, wherein the operation of the central server of issuing an alert when the sound exposure measure indicates than an alert should be sent comprises:
  comparing the sound measurement data from the first, second and third microphones; and
  issuing an alert when the sound measurement data indicates that additional sound protection measures are appropriate.

* * * * *